United States Patent
Paganon

(10) Patent No.: US 7,985,207 B2
(45) Date of Patent: Jul. 26, 2011

(54) MEDICAL IMPLANTABLE SITE HAVING A MULTI-LAYER PUNCTURE ZONE

(75) Inventor: Pascal Paganon, Serezin du Rhône (FR)

(73) Assignee: Compagnie Europeenne d'Etude et de Recherche de Dispositifs pour l'Implantation par Laparoscopie, Vienne (FR)

( * ) Notice: Subject to any disclaimer, the term of this patent is extended or adjusted under 35 U.S.C. 154(b) by 189 days.

(21) Appl. No.: 11/718,592

(22) PCT Filed: Nov. 4, 2005

(86) PCT No.: PCT/FR2005/002747
§ 371 (c)(1),
(2), (4) Date: Dec. 29, 2008

(87) PCT Pub. No.: WO2006/051192
PCT Pub. Date: May 18, 2006

(65) Prior Publication Data
US 2009/0099538 A1   Apr. 16, 2009

(30) Foreign Application Priority Data

Nov. 5, 2004  (FR) ...................... 04 11825

(51) Int. Cl.
*A61M 31/00* (2006.01)
(52) U.S. Cl. .............. 604/288.02; 604/288.01
(58) Field of Classification Search ............. 604/288.02, 604/288.01, 288.04, 116, 539, 201, 506; 128/899
See application file for complete search history.

(56) References Cited

U.S. PATENT DOCUMENTS

| | | | |
|---|---|---|---|
| 4,190,040 A | | 2/1980 | Schulte |
| 4,685,447 A | * | 8/1987 | Iversen et al. ................. 128/899 |
| 4,840,615 A | | 6/1989 | Hancock et al. |
| 4,857,053 A | | 8/1989 | Dalton |
| 6,060,639 A | | 5/2000 | Petrick |
| 2002/0049489 A1 | | 4/2002 | Herweck et al. |

* cited by examiner

*Primary Examiner* — Nicholas D Lucchesi
*Assistant Examiner* — Brooke M Matney
(74) *Attorney, Agent, or Firm* — Jason A. Bernstein; Barnes & Thornburg LLP

(57) ABSTRACT

An implantable device (1) for injecting fluid and/or for tapping fluid, the device having a housing (3) provided with a puncture zone (4) able to be transpierced by a hollow needle (5) for injecting fluid into and/or tapping fluid from a chamber (3A) provided inside the housing (3). The implantable device has a puncture zone (4) made up of at least first and second superposed flexible membranes (6, 7) mounted to be free, at least locally, relative to each other, to allow the membranes, at least locally, to move along each other, so that, once the needle (5) has been removed, the orifice formed by the needle (5) is sliced into first and second sub-orifices (6A, 7A) substantially not coinciding so as to impart a substantially leak-tight property to the puncture zone (4).

19 Claims, 2 Drawing Sheets

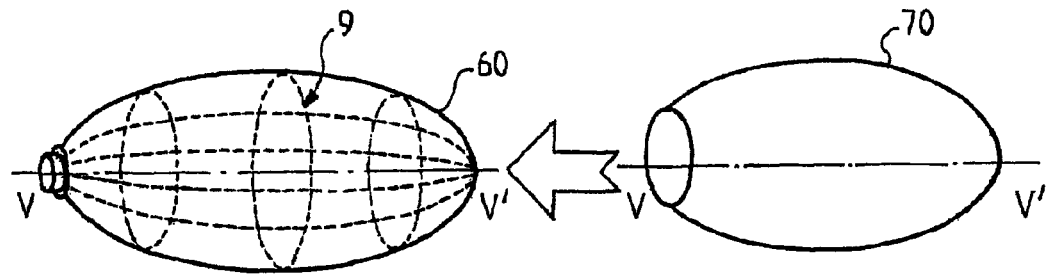
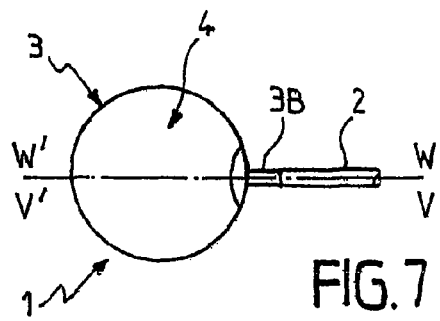
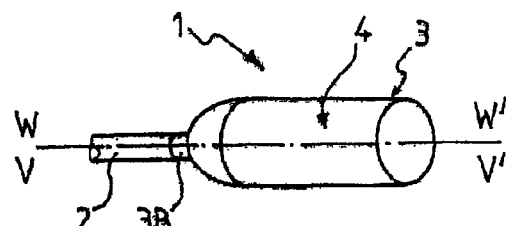
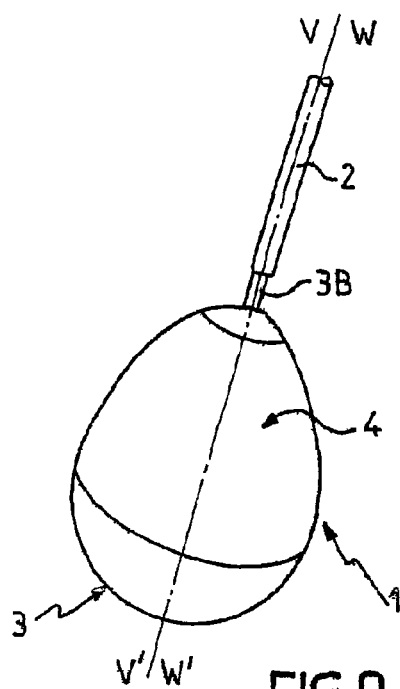
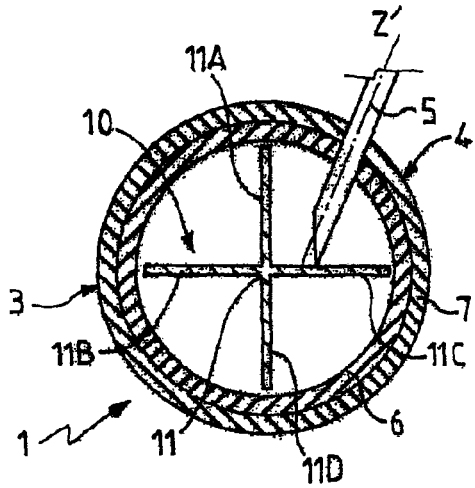
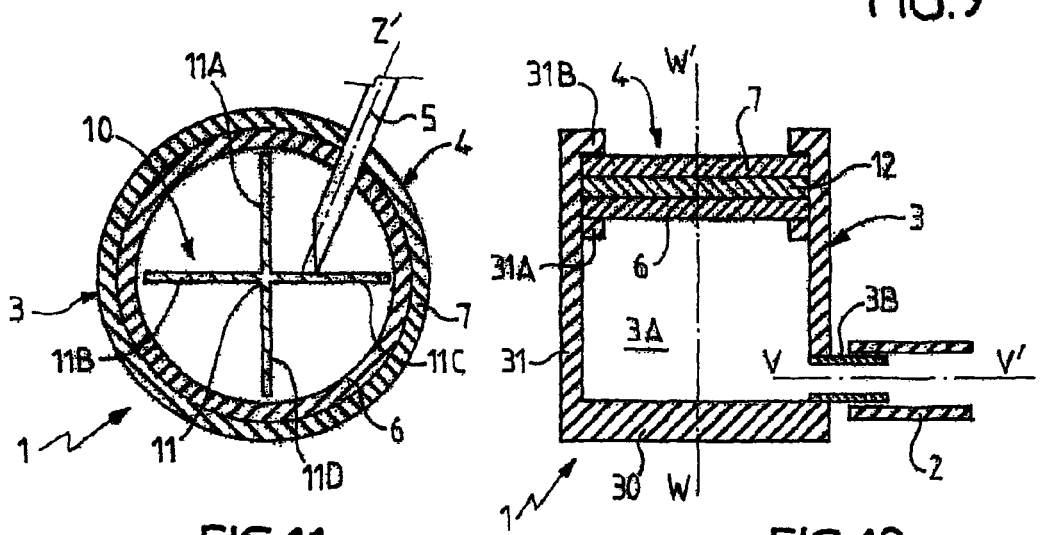

MEDICAL IMPLANTABLE SITE HAVING A MULTI-LAYER PUNCTURE ZONE

PRIORITY CLAIM

This patent application is a U.S. National Phase of International Application No. PCT/FR2005/002747, filed Nov. 4, 2005, which claims priority to French Patent Application No. 0411825, filed Nov. 5, 2004, the disclosures of which are incorporated herein by reference in their entirety.

FIELD OF THE INVENTION

The present invention relates to devices designed to be inserted surgically under the skin of a human or animal patient, for the purpose of being subsequently pierced with a hollow needle through the skin of the patient with a view to injecting substances into the body of the patient and/or to tapping substances from the body of the patient, while limiting reiterated injury to the skin at the same place. Such devices are generally referred to as "implantable sites" or as "access ports."

The present invention relates more particularly to an implantable device for injecting fluid into and/or for tapping fluid from either an organ or vessel of the body of a human or animal patient, or else an inflatable and/or deflatable compartment of a surgical implant.

The present invention also relates to a method of manufacturing an implantable device for injecting fluid into and/or for tapping fluid from either an organ or vessel of the body of a human or animal patient, or else an inflatable and/or deflatable compartment of a surgical implant.

BACKGROUND OF THE INVENTION

Known implantable sites are generally in the form of a housing having a bottom from which extend side walls whose free ends define a proximal opening. The bottom and the side walls are made of an uninterrupted and rigid material, such as titanium, in order to prevent the bottom and side walls from being transpierced by a needle. The proximal opening is closed off by a membrane made of an elastomer material forming a "septum," i.e., a puncture zone suitable for being transpierced by a needle for injecting fluid into or tapping fluid from the internal volume of the housing defined by the bottom, by the side walls, and by the membrane.

In order to ensure that the housing is properly leaktight, the membrane made of elastomer is also generally of large thickness, e.g., of thickness greater than 4 mm. The membrane is compressed laterally in uniform manner, e.g., by forced hooping or binding by means of a metal ring, so as to impart self-closure (or self-healing) properties that are sufficient. In other words, once the needle has been removed from the membrane, the membrane, by means of the continuous internal stress to which the membrane is subjected, immediately closes the hole corresponding to the needle passing through the membrane.

Although such prior art sites are generally satisfactory, these sites also suffer from certain non-negligible drawbacks.

Firstly, because of the large thickness of the membrane that is necessary in order to impart appropriate leaktightness to the housing, known implantable sites are voluminous, which can contribute to making these implantable sites uncomfortable for many patients, and in particular in patients of slight build, such as children.

In addition, known devices are generally difficult to manufacture, precisely because of the need to compress the septum-forming membrane. The operation of assembling the membrane, i.e., of inserting the membrane into a ring to compress the membrane, is thus, in general, difficult and poorly reproducible.

Finally, the need to compress the membrane significantly limits the possibilities of shaping the housing. In particular, currently known technology does not make it possible to obtain a site that can be pierced over a curved surface while also offering an excellent level of leaktightness for a large number of piercing operations (e.g., at least one thousand).

SUMMARY OF THE INVENTION

A feature of the present invention is an implantable device for injecting and/or tapping fluid that makes it possible to remedy the various above-listed drawbacks, and that offers excellent leaktightness while also being compact and while offering a large degree of freedom for the geometrical shaping of the puncture zone.

Another feature of the present invention is an implantable device for injecting and/or tapping fluid that is simple to manufacture.

Another feature of the present invention is an implantable device for injecting and/or tapping fluid that is particularly light-weight, practical, and inexpensive.

Another feature of the present invention is an implantable device for injecting and/or tapping fluid that reduces the risks and drawbacks related to bodily movements made by the patient.

Another feature of the present invention is an implantable device for injecting and/or tapping fluid that does not need to be sutured to the body of the patient.

Another feature of the present invention is an implantable device for injecting and/or tapping fluid that is particularly safe.

Another feature of the present invention is an implantable device for injecting and/or tapping fluid whose leaktightness is particularly improved.

Another feature of the present invention is an implantable device for injecting and/or tapping fluid that can be made using standard materials.

Another feature of the present invention is a method of manufacturing an implantable device for injecting and/or tapping fluid that is extremely easy to implement.

Another feature of the present invention is a method of manufacturing an implantable device for injecting and/or tapping fluid that is particularly quick and inexpensive.

The present invention provides one exemplary embodiment, an implantable device for injecting fluid into and/or for tapping fluid from either an organ or vessel of the body of a human or animal patient, or else an inflatable and/or deflatable compartment of a surgical implant, the device comprising a housing provided with a puncture zone suitable for being transpierced by a hollow needle with a view to injecting fluid into and/or to tapping fluid from a chamber provided inside the housing, the implantable device having a puncture zone made up of at least first and second superposed flexible membranes mounted to be free, at least locally, relative to each other, to allow the first and second superposed flexible membranes, at least locally, to move along each other, so that, once the needle (5) has been removed, the orifice formed by the needle (5) is sliced into first and second sub-orifices (6A, 7A) formed in respective ones of the first and second membranes (6, 7) and substantially not coinciding so as to impart a substantially leaktight property to the puncture zone (4).

The features provided by the present invention are also achieved by means of a method of manufacturing an implantable device for injecting fluid into and/or for tapping fluid from either an organ or vessel of the body of a human or animal patient, or else an inflatable and/or deflatable compartment of a surgical implant, the device having a housing with a puncture zone suitable for being transpierced by a hollow needle with a view to injecting fluid into and/or to tapping fluid from a chamber provided inside the housing, the method including a step of making the puncture zone, which step consists in superposing at least first and second flexible membranes mounted to be free, at least locally, relative to each other, so as to allow the first and second flexible membranes, at least locally, to move along each other, so that, once the needle (5) has been removed, the orifice formed by the needle (5) is sliced into first and second sub-orifices (6A, 7A) formed in respective ones of the first and second membranes (6, 7) and substantially not coinciding so as to impart a substantially leaktight property to the puncture zone (4).

BRIEF DESCRIPTION OF THE DRAWINGS

Other features and advantages of the invention will appear on reading the following description, and on examining the accompanying drawings, which are given merely by way of non-limiting illustration.

FIG. 6 shows a step, which follows the step of FIG. 5, in making the exemplary variant embodiment of the device shown in FIG. 1;

FIG. 7 is a diagrammatic perspective view showing an exemplary variant embodiment of a device of the present invention, having a first exemplary geometrical shape of the puncture zone;

FIG. 8 is a diagrammatic perspective view showing an exemplary variant embodiment of a device of the present invention, having a second exemplary geometrical shape of the puncture zone;

FIG. 9 is a diagrammatic perspective view showing an exemplary variant embodiment of a device of the present invention, having a third exemplary geometrical shape of the puncture zone;

FIG. 10 is a diagrammatic section view showing an exemplary variant embodiment of a device of the present invention, the variant differing from the variants of FIGS. 7-9, in particular, by the geometrical shape of the puncture zone; and FIG. 11 is a diagrammatic cross-section view of an exemplary variant embodiment of a device of the present invention, the device having a non-transpierceable screen disposed inside the chamber.

DETAILED DESCRIPTION OF THE INVENTION

Figure 1:
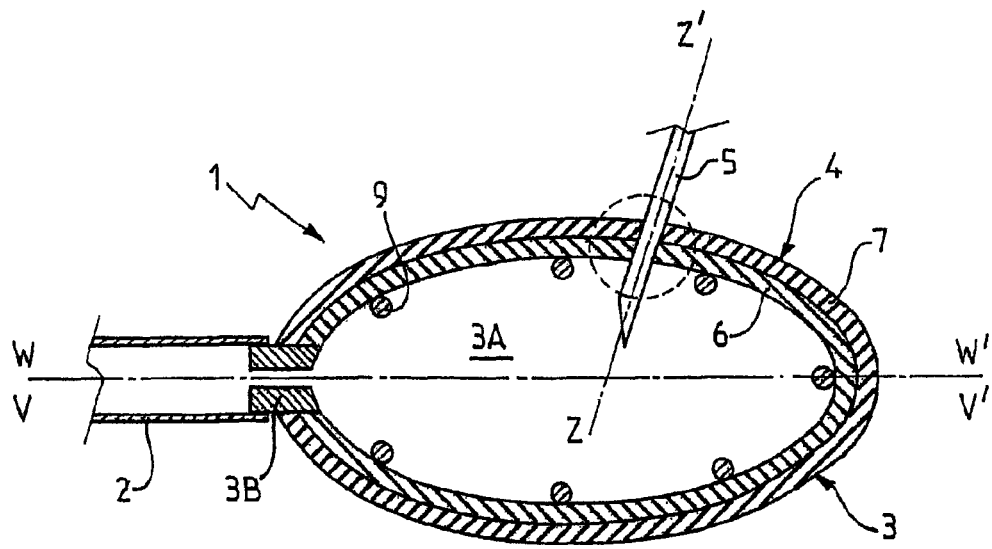
FIG. 1 is a diagrammatic longitudinal section view showing an implantable device of the present invention being perforated by a needle for the purpose of performing fluid injection or fluid removal.

The present invention relates to an implantable device 1 for injecting and/or tapping a fluid. The device, which can also be referred to as an "implantable site," is implanted surgically into the body of a patient, and, in particular, under the skin of the patient, to create an access port for inserting or for extracting fluid substances, in particular, fluid substances of the liquid type or of the pseudo-liquid type, into or from the body of the patient, who can be a human or an animal.

The implantable device 1 of the present invention can be implemented and adapted for various uses. For example, the implantable device 1 of the present invention can be designed for injecting fluid into and/or for tapping fluid from an organ or vessel of the body of a patient, and, in particular, the venous and/or arterial system of the patient. In such a use, which is known per se, the device 1 of the present invention makes it possible, for example, to inject liquid medicinal substances into a vein or artery. The device 1 of the present invention can also be adapted to feed implanted reservoirs of the insulin pump or analgesic pump types. In another exemplary embodiment, the device 1 of the present invention is specially adapted to form an artificial vein (or an artificial artery) that the practitioner, physician, or nurse can pierce as if it were a natural vein for the purpose of injecting a medicinal substance or of taking blood.

The implantable device 1 of the present invention can also be adapted to inject and/or to tap fluid, such as physiological saline solution, into and/or from an inflatable and/or deflatable compartment of a surgical implant, and, in particular, of a gastroplasty band designed to treat obesity. Such a gastric band is known per se, and the gastric band is generally formed by a flexible strip designed to be looped back around the stomach and closed substantially in the vicinities of and by the two ends, by means of a closure system, in order to reduce the diameter of the opening of the stoma. The strip can have an annular compression chamber of adjustable volume, connected via a catheter 2 to an implantable device 1 of the present invention, the device makes it possible to adjust the internal volume of the chamber, in order to adjust the diametrical expansion of the chamber. However, the device of the present invention can be used to adjust other surgical implants, such as, for example, artificial sphincters or balloons.

Reference is made below, more particularly, to a hypodermic device, i.e., a device designed to be positioned just under the skin of the patient. However, the device of the present invention can be implanted at other places of the body of the patient, and, for example, deeper.

In accordance with the present invention, the implantable device 1 comprises a housing 3 inside which a chamber is provided, the chamber is closed, preferably in liquid-tight manner. The housing 3 is advantageously provided with a duct 3B connecting the chamber 3A to the outside of the device 1. The duct 3B is preferably designed to be connected to a catheter 2, the catheter 2 is designed either to be connected to the organ or to the vessel into which fluid is to be injected or from which fluid is to be tapped, or else is connected to the inflatable/deflatable compartment of a surgical implant.

In accordance with the present invention, the housing 3 has a puncture zone 4 suitable for being transpierced by a hollow needle 5, with a view to injecting fluid into the chamber 3A provided inside the housing 3 and/or to tapping fluid from the chamber.

The puncture zone 4 has the following properties:
the puncture zone is easily transpierceable by a hollow medical needle, such as, for example, a Hubert needle; and
the puncture zone makes the chamber 3A leaktight, by preventing any leakage of liquid once the needle is removed.

In other words, the puncture zone 4 must have a self-healing property, thereby preventing the liquid present in the chamber 3A from leaking out through the hole generated by the perforation formed by the needle 5.

According to an important feature of the present invention, these self-healing and liquid-tight properties are achieved because the puncture zone 4 is made up of at least first and second superposed flexible membranes 6, 7 mounted to be free, at least locally, relative to each other, to allow the first and second superposed flexible membranes 6, 7, at least locally, to move along each other. In other words, the puncture zone 4 is attained by means of a first membrane 6 covered by at least one second membrane 7, the first and second membranes 6, 7 are independent where the first and second membranes 6, 7 form the puncture zone 4, i.e., not attached to each other, to enable the first and second membranes 6, 7 to slide relative to each other. It is precisely because of this capacity for the first and second membranes 6, 7 to move relative to each other that the orifice generated by inserting the needle 5 into the puncture zone 4 can be closed off automatically.

Since the first and second membranes 6, 7 are flexible, and preferably even elastic, each of the membranes 6, 7 deforms slightly in bending prior to being perforated, under the effect of the thrust exerted by the tip of the needle 5 along the perforation axis Z-Z'.

Figures 2, 3, 4:
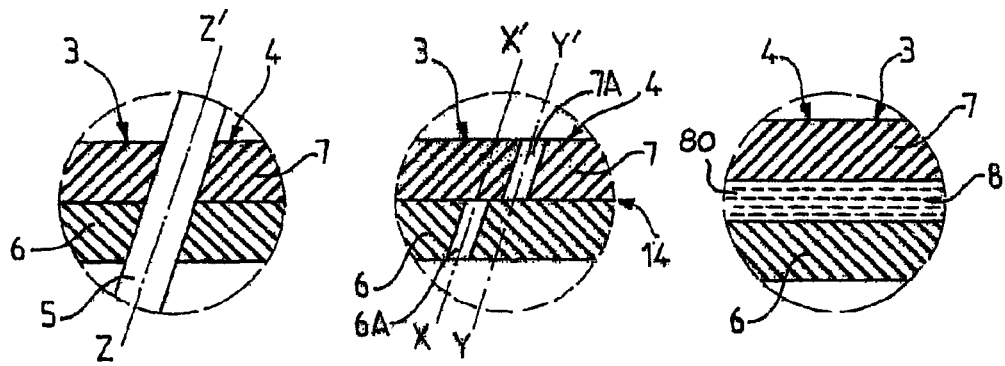
FIG. 2 is a diagrammatic section view showing an enlarged detail of FIG. 1.
FIG. 3 is a diagrammatic section view showing the FIG. 2 detail once the needle has been removed from the device.
FIG. 4 is a diagrammatic section view showing an implementation detail of a second exemplary variant device of the present invention.

The membranes 6, 7 are thus transpierced while each of the membranes 6, 7 is in a geometrical shape that is distinct from the geometrical shape that it takes up at rest, i.e., in the absence of mechanical stress from a needle. In the rest configuration, each membrane 6, 7 can be stressed in tension, or in compression, or can be subjected to almost no stress and be in a relaxed state. As shown in FIG. 3, when the needle 5 is removed from the puncture zone 4, the membranes 6, 7 resume the rest configuration. The orifice formed by the needle 5 in the puncture zone 4 then finds itself sliced into two sub-orifices 6A, 7A formed in respective ones of the first and second membranes 6, 7 and not coinciding (or substantially not coinciding) to impart a substantially leaktight property to the puncture zone 4, i.e., to prevent any leakage of fluid from the chamber 3A via the orifice formed by the needle 5.

In other words, under the effect of the membranes 6, 7 returning resiliently as allowed by the needle 5 being removed, the respective axes X-X' and Y-Y' along which the sub-orifices 6A, 7A extend become offset laterally, thereby breaking the communication between the chamber 3A and the outside. The sub-orifice 6A is closed off by the second membrane 7, while the sub-orifice 7A is closed off by the first membrane 6, each sub-orifice 6A, 7A thus forming a blind hole in the corresponding membrane. The first and second membranes 6, 7 are mounted relative to each other so that, once the needle 5 has been removed, the orifice formed by the needle 5 is sliced into first and second sub-orifices 6A, 7A formed in respective ones of the first and second membranes (6, 7) and substantially not coinciding, the sub-orifice 6A is substantially closed off by the second membrane 7, while the sub-orifice 7A is substantially closed off by the first membrane 6.

The puncture zone 4 thus resumes a leaktight configuration at the place perforated by the needle 5. The present invention makes it possible, merely by pressing two flexible walls against each other, to obtain a self-closing puncture zone 4. Naturally, it is possible, with a view to optimizing the leaktightness of the device 1, to dispose more than two independent membranes (at least locally) on one another, so as to fragment the orifice generated by the needle 5 penetrating into the puncture zone 4 into as many segments that are offset axially relative to one another, at least for some of them. It thus seems that the higher the number of membranes implemented, the higher the statistical probability of interrupting the communication between the inside of the chamber 3A and the outside, by axially offsetting the sub-orifices.

Preferably, the first and/or second membranes 6, 7 are made of an elastomer material of the silicone type. In view of the leaktight property of the silicone-on-silicone contact, it is particularly advantageous to make each membrane 6, 7 of silicone in order to optimize the leaktightness at the interface 14 between each membrane. It is also possible to implement membranes each made of a silicone whose physical properties (e.g., elasticity, hardness, etc.) differ from the physical properties of the silicones used for making the other membranes. It can be particularly advantageous for the elasticity (or the hardness) of each membrane 6, 7 to be different from the elasticity (or the hardness) of each of the other membranes in order obtain a behavior gradient over the thickness of the puncture zone 4, the gradient contributes to offsetting the sub-orifices 6A, 7A relative to each other. Naturally, it is also possible to implement any material other than silicone, and, in particular, any material suitable for being transpierced by a needle and presenting flexibility and impermeability characteristics sufficient for contributing to forming the puncture zone 4.

It is also possible, as shown in FIG. 4, to dispose between each membrane, namely, in this example, between the first and second membranes 6, 7, a layer 8 of a liquid-absorbent substance. The presence of such a layer 8 makes it possible to reinforce the leaktightness effect procured by the first and second membranes 6, 7 moving relative to each other. The layer 8 makes it possible to absorb and retain any fraction of liquid that might find its way from the first sub-orifice 6A to the second sub-orifice 7A along the interface 14 of the first and second membranes 6, 7. Preferably, the layer 8 of absorbent substance is thin enough to enable the first sub-orifice 6A to be closed off by the second membrane 7 and vice-versa (to enable the second sub-orifice 7A to be closed off by the first membrane 6). In other words, the layer 8 of absorbent substance is advantageously in the form of a film, or of a thin sheet that does not provide the leaktightness directly by itself. Advantageously, the absorbent substance from which the layer 8 is made is chosen from one of the following substances and their derivatives: super-absorbent materials, polyvinyl alcohol (PVA) foams, and hydrophilic gels. This list is non-limiting, any absorbent material of the foam or sponge type is suitable for implementing the layer 8.

Advantageously, at least one layer 80 of a lubricant substance is disposed between the first membrane 6 and the second membrane 7. The function of layer 80 is, in particular, to make it easier for the membranes 6, 7 to slide relative to each other and to make it easier for the sub-orifices 6A, 7A to be offset relative to each other, thereby making it possible to impart a leaktight property to the puncture zone 4. The layer 80 of lubricant substance is thin enough to enable the first sub-orifice 6A to be closed off by the second membrane 7 and vice versa (to enable the second sub-orifice 7A to be closed off by the first membrane 6). In other words, the layer 80 of lubricant substrate is advantageously in the form of a film, or of a thin sheet, that does not provide leaktightness directly by itself. Advantageously, the layer 80 of lubricant substance comprises a lubricant coating deposited on either one or both of the membranes 6, 7. Preferably, each face of the membranes 6, 7 that is designed to find itself facing the other membrane is covered, e.g., uniformly, with a lubricant coating (e.g., a solid coating) to form coated membranes 6, 7 so that relative sliding of the coated membranes is facilitated. For example, the lubricant layer can be based on a coating of a polymer or the like, and, in particular, based on a coating of a material known by the trade name of PARYLENE®.

Naturally, any other material or surface treatment that is known to the person skilled in the art could also be suitable. The lubricant layer could, in particular, not be formed of a solid coating attached to either of the membranes 6, 7 as described above, but rather be constituted by a thin film of (viscous) fluid interposed between the membranes 6, 7.

It is also possible to use a substance that is both absorbent and lubricant, in order to obtain a dual-purpose layer 8, 80 (cf. FIG. 4).

Figure 5:
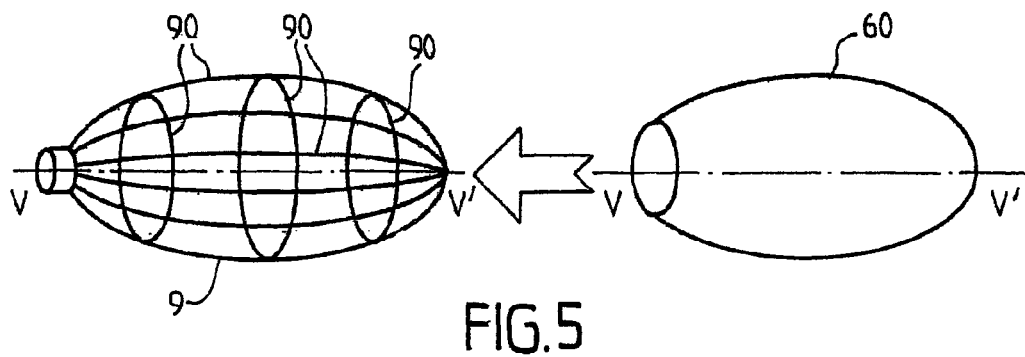
FIG. 5 shows one step in making the exemplary variant embodiment of the device shown in FIG. 1.

In a preferred exemplary embodiment, the housing 3 includes a perforated skeleton 9, i.e., an open framework forming the structure of the housing 3 and imparting to the housing its overall shape. The skeleton 9 advantageously has rigid or semi-rigid properties, and is preferably made of a material that is substantially non-transpiercable by the needle 5. As shown in FIGS. 5 and 6, the skeleton 9 advantageously comprises a latticework of wires or filaments 90, e.g., made of metal or of substantially rigid plastic. The latticework can, for example, be made by means of titanium wires, or result from molding a polymer. Advantageously, the skeleton 9 forms a three-dimensional structure that is convex in overall shape, and over which membranes 6, 7 are designed to be stretched. To this end, the first and second membranes 6, 7 are preferably in the form of respective ones of first and second first extensible sheaths 60, 70. The first sheath 60 covers the skeleton 9 to form a sheathed skeleton 9A, over which the second sheath 70 (cf. FIG. 6) is force-fitted, by elastic deformation.

Advantageously, the first sheath 60 is also force fitted, by elastic deformation, over the skeleton 9. In other words, in the preferred embodiment shown in FIGS. 5 and 6, the skeleton 9 forms a reinforcing framework serving to support at least two membranes 6, 7 which are successively fitted over the skeleton 9 to take on the general shape of the skeleton 9, by elastic deformation, in the manner of a sock put on a foot. The sheaths 60, 70 can be closed pouches that are open at one end only, so that the sheaths 60, 70 are suitable for fitting over the reinforcing framework 9, or else in the form of sleeves, i.e., sheaths that are open at both opposite ends. Naturally, the sheaths 60, 70 are of a general shape close to the shape of the skeleton 9 so that the skeleton 9 being covered by the sheaths 60, 70 does not give rise to creases or to zones that are too slack, but rather facilitates substantially uniform tensioning of each sheath 60, 70 over the skeleton 9. The membranes 6, 7 are thus stretched over the reinforcing framework formed by the skeleton 9. However, it is quite possible for the membranes 6, 7 to be tensioned merely temporarily as the membranes 6, 7 are placed on the skeleton 9, and are then in a relaxed state (i.e., a state in which stresses are relaxed), or indeed in a compressed state, once the membranes 6, 7 are positioned on the skeleton 9.

The superposed sheaths 60, 70 cooperating with the skeleton 9 make it possible to form the puncture zone 4 because the needle 5 can transpierce the stack of membranes 6, 7 into the orifices provided in the surface of the skeleton 9, which orifices are defined, for example, by metal meshing or latticework that advantageously forms the skeleton 9.

Advantageously, the duct 3B connecting the chamber 3A to the outside of the device 1 extends longitudinally along a first axis V-V', the puncture zone 4 is substantially symmetrical relative to a second axis W-W', that is substantially parallel to and preferably coincides with the first axis V-V'. In this exemplary embodiment, which corresponds to the various variants shown in FIGS. 1-9 and 11, the housing 3, and preferably the puncture zone 4, are preferably substantially circularly symmetrical about the second axis W-W', which axis coincides with the first axis V-V' in the direction in which the duct 3B extends.

Such an implantable device 1, whose puncture zone 4 is circularly symmetrical, is particularly comfortable for the patient because the implantable device 1 does not need to be sutured to the biological tissues of the patient on being implanted. The suturing performed in the prior art is justified by the difficulties that could arise if the device 1 were to turn over under the skin of the patient, e.g., due to movements of the patient. Such turning over could give rise to the puncture zone 4 being masked, i.e., to the puncture zone 4 being impossible for a needle 5 to perforate it through the skin of the patient. Such a problem is solved completely by the device 1 of the variants of FIGS. 1-9 since, even if such a device does turn over under the skin of the patient, a portion of the puncture zone 4 always remains accessible to the needle 5 by means of the circular symmetry of the puncture zone 4.

Advantageously, the puncture zone 4 is spherical in overall shape, as is shown in FIG. 7. Such a spherical puncture zone 4 can be obtained by implementing a skeleton 9 that is spherical in overall shape, and over which a series of sheaths are fitted, the sheaths having the form of spherical pouches each having one opening and being suitable for being distended so that each sheath can be fitted successively over the spherical skeleton.

In another exemplary embodiment, corresponding to FIGS. 1-6, the puncture zone 4 is ovoid in overall shape, the major axis of symmetry W-W' extending substantially in the same direction as the direction V-V' in which the duct 3B extends. Such an ovoid puncture zone 4 is obtained, for example, as shown in FIGS. 5 and 6, by implementing an ellipsoidal latticework covered with a plurality of pouches that have ellipsoidal shapes that are complementary to the shape of the latticework, so as to obtain an ovoid housing 3. Such an ovoid housing is particularly easy to insert under the skin of a patient, and is generally particularly well tolerated by the patient.

In another exemplary embodiment, the puncture zone 4 is substantially pear-shaped as shown in FIG. 9. Preferably, the axis of symmetry of the pear-shaped zone 4 W-W' coincides with the axis V-V' along which the duct 3B extends. In a manner analogous to the manner described above, the pear-shaped zone 4 can be obtained by covering a pear-shaped latticework with flexible pouches that have shapes complementary to the shape of the latticework.

In another exemplary embodiment, corresponding to FIG. 8, the puncture zone 4 is cylindrical in overall shape. Such a cylindrical puncture zone 4 can, for example, be obtained by implementing a skeleton 9 that is cylindrical and over which a plurality of sleeves that are cylindrical and open at both opposite ends are fitted such that the sleeves are superposed on one another. It is also possible to imagine covering the cylindrical skeleton of the device corresponding to FIG. 8 with pouches that have a single opening, unlike the above-mentioned sleeves that have two openings.

Advantageously, a screen 10 made of a material that is not transpierceable by the hollow needle 5 is disposed inside the housing, in order to prevent the housing 3 from being perforated through to the other side during transpiercing by the needle 5 (cf. FIG. 11). The screen 10 prevents the needle 5 from exiting from the chamber 3 to the outside of the device 1, it being possible for such exiting to cause injury to the biological tissues around the device 1. In particular, the screen 10 is designed as a function of the shape of the puncture zone 4, to allow piercing that is effective and safe to be performed at any point on the puncture zone 4. Advantageously, the screen 10 comprises a bladed wheel 11 that is shaped and positioned such that the blades 11A, 11B, 11C, 11D extend substantially radially about the axis of symmetry W-W' of the puncture zone 4. Advantageously, there are at least four blades 11A, 11B, 11C and 11D that are preferably uniformly spaced apart angularly. Naturally, it is quite possible to imagine providing a lower or a higher number of blades, or even some other type of screen 10. In addition, the screen 10 is shaped to enable fluid communication or circulation to be established inside the chamber 3A. For example, in the example shown in FIG. 10 in which the screen 10 is formed by a wheel having four blades 11A, 11B, 11C, 11D, the four compartments defined inside the chamber 3A by the blades 11A, 11B, 11C, 11D are not leaktight, and they are all in fluid communication, even indirectly, with one another. For this purpose, it is, for example, possible to dimension blades so that they do not fit snugly against the first membrane 5 forming the outline of the chamber 3A (in the exemplary embodiment shown in FIG. 10). The screen 10 can float freely inside the chamber 3A, or optionally can be held in position by means of a fastening system. Naturally, the use of a screen 10 is optional.

The devices 1 described above are circularly symmetrical. However, it is quite possible for the device 1 to have a more conventional configuration, as shown in FIG. 10. In which case, the housing 3 comprises a bottom 30, e.g., a disk-shaped bottom, from which a side wall 31 extends. The bottom 30 and the wall 1 are preferably made of a material that is not transpierceable by a needle 5. Opposite from the bottom 30, the side wall 31 defines an opening closed off by a puncture zone 4 formed by a superposition of at least two and, for example, three (as shown in FIG. 11) membranes 6, 7, 12. In accordance with the general concept of the present invention, the first, second, and third membranes 6, 7, 12 are mounted to be free relative to one another and, for example, are held in position at their peripheries only, by the presence of a bottom rim 31A and of a top rim 31B, the rims extending inwards from the side wall 31, and being designed to clamp the stack of membranes 6, 7, 12 between them. Conventionally, the device shown in FIG. 11 is provided with a duct 3B extending from the side wall 3A in a direction V-V' that is perpendicular to the axis of symmetry W-W' of the housing 3.

The present invention also relates to a method of manufacturing an implantable device 1 for injecting fluid into and/or for tapping fluid from either an organ or vessel of the body of a human or animal patient, or else an inflatable and/or deflatable compartment of a surgical implant, the device 1 comprising a housing 3 provided with a puncture zone 4 to be transpierced by a hollow needle 5 for injecting fluid into and/or for tapping fluid from a chamber 3A provided inside the housing 3.

According to an important feature of the present invention, the method includes a step of making the puncture zone 4, the step comprises superposing at least first and second flexible membranes 6, 7 mounted to be free, at least locally, relative to each other, to allow the first and second flexible membranes 6, 7, at least locally, to move along each other, so that, once the needle 5 has been removed, the orifice formed by the needle 5 is sliced into first and second sub-orifices 6A, 7A formed in respective ones of the first and second membranes 6, 7 and substantially not coinciding so as to impart a substantially leaktight property to the puncture zone 4.

Advantageously, the first and second membranes 6, 7 are mounted relative to each another so that the first sub-orifice 6A is substantially closed off by the second membrane 7 and vice versa once the needle 5 is removed.

Advantageously, the method of the present invention includes an interposition step comprising interposing between each membrane 6, 7 a layer 80 of lubricant substance. Preferably, the interposition step comprises a deposition step of depositing a coating of lubricant (such as, for example, PARYLENE®) on either one or both of the membranes 6, 7, the coating is preferably uniform and secured to the membrane 6, 7 in question. It is also possible, as described above, for the lubricant layer 80 to be in the form of thin viscous film independent from the membranes 6, 7 and interposed between the membranes 6, 7.

Advantageously, the method of the present invention includes a manufacturing step for manufacturing the housing 3, the step consists of providing or manufacturing a perforated skeleton 9. Advantageously, the step of making the puncture zone 4 comprises providing or manufacturing first and second extensible sheaths 60, 70 that form respective ones of the first and second membranes 6, 7 and in covering the skeleton 9 with the first sheath 60 to form a sheathed skeleton 9A, and then in force-fitting the second sheath 70 over the sheathed skeleton.

The above-described method can advantageously constitute a method of manufacturing an implantable device for injecting inflation fluid into and/or tapping inflation fluid from an inflatable and/or deflatable compartment of a gastroplasty band designed for treating obesity. The method of the present invention can alternatively constitute a method of manufacturing an implantable device for injecting a medicinal substance into a vein or an artery and/or for removing blood from the vein or artery, the device 1 thus forming an artificial vein or an artificial artery.

The present invention makes it possible to obtain an implantable site offering excellent leaktightness without implementing a large thickness of silicone which is necessary for prior art septa. The principle of the present invention makes it possible, by means of a stack of very thin membranes, to obtain a puncture zone that, in spite of its small thickness, offers an excellent self-healing property.

The present invention also makes it possible to solve the problem of leaktightness of an implantable site whose puncture zone is circularly symmetrical. The geometrical shapes of such sites prevent prior art solutions to that problem from being used, such prior solutions involving uniformly and radially compressing a thick block of silicone.

Finally, the present invention makes it possible, extremely simply, to obtain an implantable device 1 that offers the above-mentioned advantages, by means of a manufacturing method that is easy and quick to implement.

The present invention can be used in designing, manufacturing, and using implantable devices for injecting and/tapping fluid.

The invention claimed is:

1. An implantable device for injecting fluid into or for tapping fluid from either an organ or vessel of the body of a human or animal patient, or an inflatable and/or deflatable compartment of a surgical implant, comprising:
   a housing having a puncture zone suitable for being transpierced by a hollow needle for injecting fluid into and/or tapping fluid from a chamber inside the housing,
   wherein the puncture zone is made up of at least a first and a second superposed flexible membranes mounted to be free, at least locally, relative to each other, to allow the first and the second superposed flexible membranes, at least locally, to move along each other, so that, once the needle has been removed, the orifice formed by the needle is sliced into a first sub-orifice formed in the first membrane and a second sub-orifice formed in the second membrane and substantially not coinciding so as to impart a substantially leaktight property to the puncture zone, wherein the housing further comprises a perforated skeleton, the skeleton having a inner side and an outer side, the first membrane being provided in the form of a first extensible sheath and the second membrane being provided in the form of a second extensible sheath, the first sheath covering the skeleton to form a sheathed skeleton, and the second sheath is force-fitted over the first sheath and, wherein the first and second membranes are each on the same side of the skeleton.

2. The device of claim 1, wherein the first and second membranes are mounted relative to each other such that the first sub-orifice is substantially closed off by the second membrane once the needle has been removed.

3. The device of claim 1, wherein the skeleton comprises a latticework of substantially rigid wires or filaments.

4. The device of claim 1, wherein the puncture zone has a shape selected from the group consisting of a substantially spherical shape, a substantially ovoid shape, a substantially pear-shaped shape, and a substantially cylindrical shape.

5. The device of claim 1, further comprising at least one layer of a liquid absorbent substance is disposed between the first membrane and the second membrane.

6. The device of claim 5, wherein the absorbent substance is selected from the group consisting of super-absorbent materials, polyvinyl alcohol (PVA) foams, hydrophilic gels and derivatives of the foregoing.

7. The device of claim 1, further comprising at least one layer of a lubricant substance is disposed between the first membrane and the second membrane.

8. The device of claim 7, wherein the layer of lubricant substance comprises a coating of lubricant deposited on either one or both of the membranes.

9. The device of claim 1, wherein the first and the second membranes are based on an elastomer material of the silicone type.

10. The device of claim 1, forming an implantable device for injecting inflation fluid into and/or for tapping inflation fluid from an inflatable and/or deflatable compartment of a gastroplasty band.

11. The implantable device of claim 1, for injecting a medicinal substance into a vein or artery and for taking blood from the vein or artery, thereby forming an artificial vein or an artificial artery.

12. A method of manufacturing an implantable device for injecting fluid into and/or for tapping fluid from either an organ or vessel of the body of a human or animal patient, or an inflatable and/or deflatable compartment of a surgical implant, the method comprising:

a) providing a housing having a puncture zone suitable for being transpierced by a hollow needle for injecting fluid into and/or tapping fluid from a chamber inside the housing; and, b) superimposing at least first and second flexible membranes mounted to be free, at least locally, relative to each other, to allow the first and second flexible membranes, at least locally, to move along each other, so that, once the needle has been removed, the orifice formed by the needle is sliced into first sub-orifice formed in the first membrane and second sub orifice formed in the second membrane and substantially not coinciding so as to impart a substantially leaktight property to the puncture zone, the housing further having a perforated skeleton, the skeleton having a inner side and an outer side, the first membrane being provided in the form of a first extensible sheath and second membrane being provided in the form of a second extensible sheath, the first sheath covering the skeleton to form a sheathed skeleton, and the second sheath is force-fitted over the first sheath, wherein the first and second membranes are each on the same side of the first extensible sheath and are on the same side of the skeleton.

13. The method of claim 12, wherein the first and second membranes are mounted relative to each other such that the first sub-orifice is substantially closed off by the second membrane once the needle has been removed.

14. The method of claim 13, further comprising c) providing or manufacturing a perforated skeleton, wherein the puncture zone is provided or manufactured in the first and second extensible sheaths, covering the skeleton with the first sheath to form a sheathed skeleton, and then force-fitting the second sheath over the sheathed skeleton.

15. The method of claim 12, further comprising c) providing or manufacturing a perforated skeleton, wherein the puncture zone is provided or manufactured in the first and second extensible sheaths, covering the skeleton with the first sheath to form a sheathed skeleton, and then force-fitting the second sheath over the sheathed skeleton.

16. The method of claim 12, further comprising a layer of lubricant substance is interposed between each membrane.

17. The method of claim 16, further comprising a coating of lubricant is deposited on either one or both of the membranes.

18. The method of claim 12, further comprising a method of manufacturing an implantable device for injecting inflation fluid into and/or tapping inflation fluid from an inflatable and/or deflatable compartment of a gastroplasty band.

19. The method of claim 12, further comprising a method of manufacturing an implantable device for injecting a medicinal substance into a vein or an artery and/or for removing blood from the vein or artery, the device thus forming an artificial vein or an artificial artery.

* * * * *